United States Patent [19]

Hibert et al.

[11] Patent Number: 5,508,280

[45] Date of Patent: Apr. 16, 1996

[54] 5H-DIBENZO (A,D) CYCLOHEPTENES AS MUSCARINIC RECEPTOR ANTAGONISTS

[75] Inventors: Marcel Hibert, Eschau; Luc Van Hijfte, Wangen; Mary Richards, Pfulgriesheim; Paul Moser, Strasbourg, all of France

[73] Assignee: Merrell Pharmaceuticals Inc., Cincinnati, Ohio

[21] Appl. No.: 380,472

[22] Filed: Jan. 30, 1995

Related U.S. Application Data

[63] Continuation of Ser. No. 949,842, Nov. 17, 1992, abandoned.

[30] Foreign Application Priority Data

May 18, 1990 [EP] European Pat. Off. ........... 90401332.3

[51] Int. Cl.⁶ .................... C07D 211/70; A61K 31/495; A61K 31/445; A61K 31/135
[52] U.S. Cl. .................. 514/255; 514/325; 514/655; 544/380; 546/203; 564/366; 564/389; 564/391; 568/308; 570/183
[58] Field of Search ........................ 544/380; 546/203; 564/366, 389, 391; 514/255, 325, 655

[56] References Cited

U.S. PATENT DOCUMENTS

| | | | |
|---|---|---|---|
| 3,436,391 | 4/1969 | Holm | 546/203 |
| 4,816,456 | 3/1989 | Sumners | 544/361 |
| 5,250,681 | 10/1993 | Shoji et al. | 540/577 |
| 5,302,602 | 4/1994 | Oshima et al. | 540/604 |
| 5,393,890 | 2/1995 | Syoji et al. | 546/80 |

FOREIGN PATENT DOCUMENTS

| | | |
|---|---|---|
| 0357956 | 3/1990 | European Pat. Off. . |
| 3558M | 9/1965 | France . |
| 2100873 | 3/1972 | France . |
| 2185413 | 1/1974 | France . |
| 91-17973 | 11/1991 | France . |

OTHER PUBLICATIONS

*The Bantam Medical Dictionary*, (John Wiley & Sons, Publishers), p. 265 (1981).

*Advanced Organic Chemistry* by Jerry March (2nd Ed.), pp. 864–865 (1977).

Engelhardt et al, *J. Med. Chem.* II, pp. 325–332 (1968).

Primary Examiner—Emily Bernhardt
Attorney, Agent, or Firm—Carolyn D. Moon

[57] ABSTRACT

This invention relates to novel derivatives of 5H-dibenzo (a,d)cycloheptenes, to the processes for their preparation, to their muscarinic receptor antagonist properties and to their end-use application for treating Parkinson's Disease, tardive dyskinesia, and motion sickness.

4 Claims, No Drawings

5H-DIBENZO (A,D) CYCLOHEPTENES AS MUSCARINIC RECEPTOR ANTAGONISTS

This is a continuation of application Ser. No. 07/949,842, filed Nov. 17, 1992, now abandoned which is herein incorporated by reference.

This invention relates to novel derivatives of 5H-dibenzo [a,d]cycloheptenes, to the processes for their preparation, to their muscarinic receptor antagonist properties and to their end-use application for treating Parkinson's Disease, tardive dyskinesia, and motion sickness.

FR-A-2 100 873 discloses that the compound 5-(3-dimethylamine-1-propylidene)-5H-dibenzo [a,d] cycloheptene is used in the treatment of muscle hyperactivity.

EP-A-0 357 956, discloses that certain dihydrobenzocycloheptiliden-ethyl-piperazine derivatives possess vasodilatory activity.

FR-A-0 946 957 discloses certain dibenzocycloheptenes having piperzinyl and aminoalkylidene substitutents are used for a variety of indications including antispasmodics, antidepressants, antiserotonin agents and antihistaminics, tranquilizers or stimulants of the central nervous system.

FR-A-2185413 discloses dibenzocycloheptene derivatives which can be used as tranquilizers or sedatives.

More specifically this invention relates to compounds of the formula

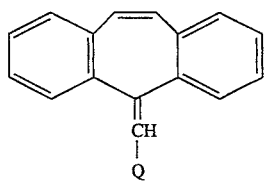

I and the pharmaceutically acceptable salts thereof, wherein Q is

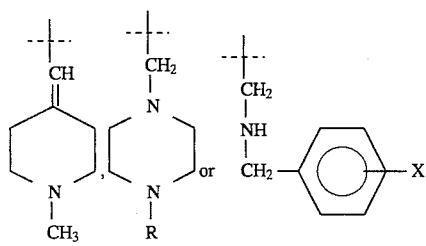

with R being H or $CH_3$, and X is H, $C_{1-6}$ alkyl, halogeno or $C_{1-6}$ alkoxy.

As used herein the terms $C_{1-6}$ alkyl and alkoxy include the straight, branched chain and cyclized manifestations of saturated aliphatic hydrocarbons having up to six carbon atoms such as, for example, methyl, ethyl, propyl, cyclopropyl, t-butyl, pentyl and hexyl and the ether analogs thereof. The term halogen particularly includes chlorine, bromine or fluorine. For

wherein X is other than H, it is preferred that the substituent be in the para position of the phenyl moiety, although the ortho- and meta-substituted compounds are also contemplated as within the scope of claimed compounds.

Contemplated as equivalents of the compounds of this invention (I) are those analogs which contain $C_{1-6}$ alkyl, halogen, $CF_3$, OH, $C_{1-6}$ alkoxy and alkanoyloxy substituents in one or both of the benzenoid moieties of the 5H-dibenzo [a,d] cycloheptenes nucleus. In those instances wherein X is other than H, it is preferred that the substituent be located in the para position of the phenyl moiety.

The compounds of Formula I are basic in nature and form acid addition salts with acids generally found beneficial in pharmaceutical preparations of such basic compounds. Such salts include those formed with such acids as hydrochloric, hydrobromic, sulfuric, phosphoric, maleic, oxalic, succinic, methyl sulfonic, tartaric and such other acids generally known for such purposes.

The compounds of this invention may be prepared from known dibenzo [a,d] cyclohepten-5-ones by processes and techniques analogously known in the art. These processes may be schematically represented in the following reaction scheme.

Reaction Scheme A

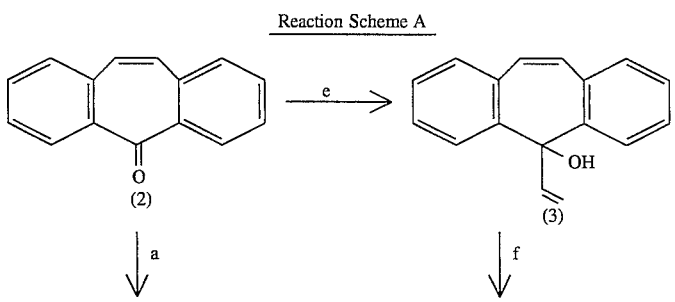

-continued
Reaction Scheme A

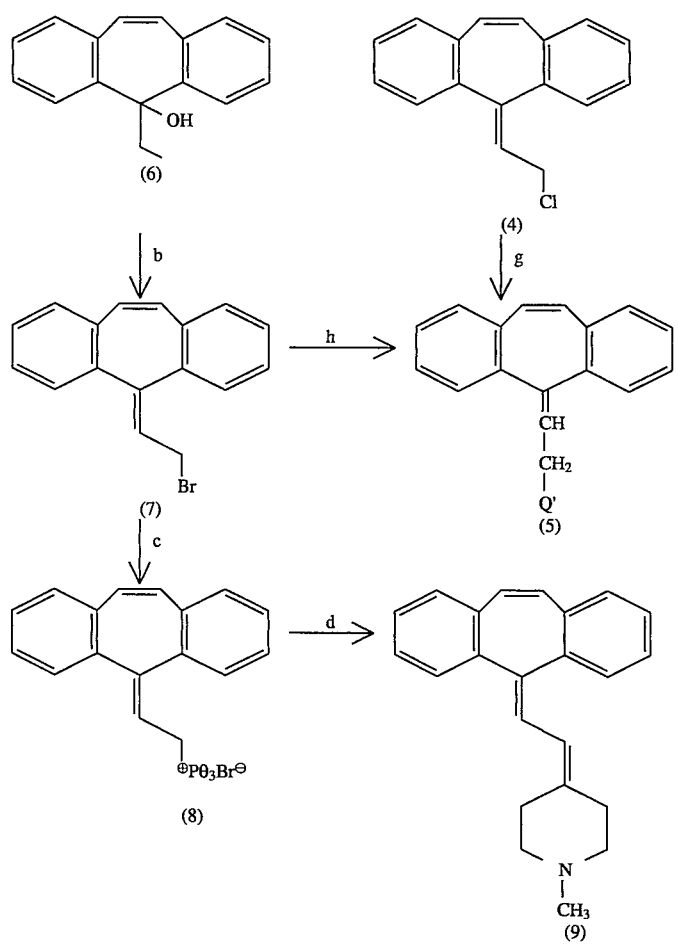

wherein Q' represents

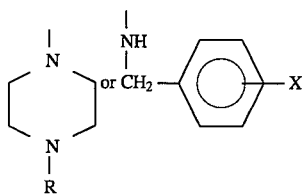

and R and CH$_2$—(C$_6$H$_4$—)X are as defined for Formula I, and PØ$_3$Br is the bromide salt of triphenylphosphonium.

Step (a) of the reaction scheme involves a Grignard-type reaction with the dibenzo [a,d] cyclohepten-5-ones (2) with an ethyl magnesium bromide to produce the expected carbinol (6) which is converted to its 5-bromo methyl-5-ene derivative by sequential reactions with glacial acetic acid and acetylchloride, followed by N-bromosuccinimide (NBS) in the presence of catalytic quantities of benzoylperoxide (Step b). The so-produced 2-bromo ethylidene derivatives (7) are converted to their 2-triphenyl phosphonium bromide ethylidene derivatives (8) by reaction with triphenylphosphine under an inert gas. Compound (8), as its bromide salt, is reacted with butyl lithium and the resulting lithio derivative, when reacted with 1-methyl-4-piperidone forms the desired derivative.

Alternatively, the 2-bromo-ethylidene derivatives (7) may be reacted with N-methyl piperazine (Step H) to produce the expected final compound.

Using Step E, the ketones of Formula (2) may be subjected to a Grignard-type reaction with vinyl magnesium bromide and the resulting alcohols (3) are reacted with thionylchloride to form the dehydrated 5-(2-chloroethylidene) derivatives (4) which when reacted with the appropriate amine (e.g., X-substituted benzylamine or 1-piperazine carboxaldehyde) produces the desired compounds of Formula (5).

The foregoing processes are illustrated by the following examples.

EXAMPLE 1

5-(2'-Benzylamino-ethylidene)-5H-dibenzo[a,d]cycloheptene

STEP A:
5-HYDROXY-5-VINYL-5H-DIBENZO[a,d]CYCLOHEPTENE

To a solution of benzosuberenone (10 g, 48 mmol) in anhydrous tetrahydrofuran under argon at 0° C. is added vinyl magnesium bromide (62 ml, 1 mol in tetrahydrofuran). The mixture is allowed to warm to room temperature, and is stirred for 3 hours. Brine is added, the aqueous phase is extracted with ether. The combined organic phases are dried over magnesium sulfate, filtered and concentrated in vacuo, to obtain 10 g of the title compound as a pale yellow oil.

STEP B:
5-(2'-CHLOROETHYLIDENE)-5H-DIBENZO[a,d]CYCLOHEPTENE

To a solution of 5-hydroxy-5-vinyl-5H-dibenzo[a,d]cycloheptene (11 g, 48 mmol) in dichloromethane (300 ml) at 0° C. under argon atmosphere is added dropwise thionylchloride (62 mmol, 4.6 ml). The mixture is then stirred for 4 hours at room temperature. Water (100 ml) is added, the organic phase is removed and the aqueous phase is extracted with ether (350 ml). The combined organic phases are washed with water, saturated aqueous sodium bicarbonate and brine, dried over magnesium sulfate, filtered and concentrated in vacuo. The residue is taken up in 150 ml of hot isooctane, the insoluble material is removed by decantation and the solution is cooled to room temperature, whereby the expected product crystallizes. The crystalline material is filtered, washed with isooctane and dried: 9 g of the pure title compound is obtained.

STEP C:
5-(2'-BENZYLAMINO-ETHYLIDENE)-5H-DIBENZO[a,d]CYCLOHEPTENE

To a solution of 5-(2'-chloroethylidene)-5H dibenzo[a,d] cycloheptene (1.25 g, 5 mmol) in acetonitrile (30 ml) is added benzylamine (1.6 g, 15 mmol) and the mixture is refluxed for 4 hours under argon atmosphere. The solution is concentrated in vacuo, the residue is taken up in water, and the solution is basified with concentrated aqueous sodium bicarbonate. The water phase is extracted with ethyl acetate. The organic mixture is dried over magnesium sulfate, filtered and concentrated in vacuo. The residue (1.2 g) is dissolved in ether and a solution of oxalic acid (0.5 g) in tetrahydrofuran is added. The oxalate salt precipitates, and is recrystallized twice from ethanol, m.p. 209° C.

In a similar manner, by substituting benzylamine with equivalent amounts of the appropriately X-substituted benzylamine and by following substantially the same procedure there is produced the desired compounds wherein X is a $C_{1-6}$ alkyl or alkoxy or halogeno.

EXAMPLE 2

5-(2'-N-Piperazinyl-ethylidene)-5H-dibenzo[a,d]cycloheptene

To a solution of 5-(2'-chloroethylidene)-5H-dibenzo [a,d] cycloheptane (2.5 g, 10 mmol) in acetonitrile (50 ml) under an argon atmosphere is added 1-piperazine carboxaldehyde (2.3 g, 20 mmol), and the mixture is refluxed for 4 hours. The solvent is removed in vacuo, the residue is taken up in water; the mixture is basified with saturated aqueous sodium bicarbonate and extracted with ethyl acetate. The combined organic portions are dried over magnesium sulfate, filtered and concentrated in vacuo. The residue is taken up in methanol, sodium hydroxide (2 g) is added and the mixture is refluxed overnight. The solvent is removed in vacuo, the residue is taken up in water and extracted with ethyl acetate. The organic phase is dried over magnesium sulfate, filtered and concentrated in vacuo, to give a pale yellow oil. The residue is dissolved in tetrahydrofuran and a solution of oxalic acid (1.6 g) in tetrahydrofuran is added. The oxalate salt of the title compound is filtered off and recrystallized twice from ethanol, m.p. 160° C.

EXAMPLE 3

5-(2'-N-[N'-Methyl-piperazinyl]-ethylidene)-5H- dibenzo[a,d]-cycloheptene

STEP A:
5-ETHYL-5H-DIBENZO[a,d]CYCLOHEPTENE-5-OL

To 150 mmol of ethyl magnesium bromide in 150 ml of ether are added 10 g (48.5 mmol) of dibenzosuberenone in 250 ml of ether at 0° C. After 3 hours at about 10° C., the mixture is cooled in an ice bath and 40 ml of saturated aqueous ammonium chloride are added slowly. Extractions of the aqueous phase with ether affords 10.75 g of a yellow oily residue. Purification by flash chromatography yields 8.5 g (74%) of the expected product.

STEP B:
5-ETHYLIDENE-5H-DIBENZO[a,d]CYCLOHEPTENE 8.5 g of 5-ethyl-5H-dibenzo[a,d]cycloheptene- 5-ol are dissolved in 70 ml of glacial acetic acid and 14 ml of acetyl chloride and the mixture is stirred and warmed at 95° C. overnight. Evaporation to dryness leads to a red oily residue which is dissolved in ethyl acetate, washed with water and dried on sodium sulfate. Evaporation affords 8.26 g of a crude oil which is purified by flash chromatography (cyclohexane) yielding 8.27 g (78%) of the pure title compound. A 96.5% yield can be obtained with a 3 days reaction time.

STEP C:
5-(2'-BROMOETHYLIDENE)-5H-DIBENZO[a,d]CYCLOHEPTENE

To 2.8 g (12.8 mmol) of 5-ethylidene-5H-dibenzo [a,d] cycloheptene dissolved in 150 ml of carbon tetrachloride is added 1 equivalent of dry N-bromosuccinimide and a few milligrams of benzoylperoxide. The mixture is warmed and lightened with a 150 W lamp and after a few minutes the reaction is finished as indicated by succinimide floating at the surface. The mixture is cooled, filtered and evaporated to dryness. NMR indicates an almost quantitative yield. The compound is used as such, without further purification.

STEP D:
5-(2'-N-[N'-METHYL-PIPERAZINYL]-ETHYLIDENE)-5H- DIBENZO[a,d]-CYCLOHEPTENE 2.42 g (8.15 mmol) of 5-(2'-bromoethylidene)-5H-dibenzo[a,d]cycloheptene, 1.85 ml (2 equivalents) of N-methylpiperazine and 3 equivalents of potassium carbonate are mixed in 20 ml of dimethylformamide and warmed at 60° C. for 20 hours under an argon atmosphere. The resulting mixture is evaporated to dryness, dissoluted in dichloromethane, washed with water, dried on sodium sulfate and evaporated to afford 2.47 g of a crude yellow oil. Purification by flash chromatography (dichloromethane/methanol: 95/5) gives 1.77 g (68.6%) of the expected product. Crystallization from tetrahydrofuran affords the title compound as a dioloxate, having a melting point of 219° C.

EXAMPLE 4

5-(2'-[N-Methyl-4-piperidinylidene]-ethylidene)- -5H-dibenzo[a,d]cycloheptene

STEP A:
[5-(2'-TRIPHENYLPHOSPHONIUM ETHYLIDENE)-5H-DIBENZO[a,d]CYCLOHEPTENE] BROMIDE

To 5-(2'-bromoethylidene)-5H-dibenzo[a,d]cycloheptene (2 g, 6.73 mmol) dissolved in 20 ml of dry toluene is added 1.765 g (1 equivalent) of triphenylphosphine is added. A complete dissolution is observed, followed by precipitation. The mixture, under an argon atmosphere, is refluxed overnight under argon and then cooled. The precipitate is filtered off, washed with toluene and ether and dried under vacuum to yield 3.76 g of 5-(2'- triphenylphosphonium ethylidene)-5H-dibenzo[a,d]cycloheptene bromide, as a white solid, which is used as such in the next step.

STEP B:
5-(2'-[N-METHYL-4-PIPERIDINYLIDENE]-ETHYLIDENE) -5H-DIBENZO[a,d]CYCLOHEPTENE

To [5-(2'-triphenylphosphonium ethylidene)-5H- dibenzo[a,d]cycloheptene] bromide (3.76 g, 6.72 mmol) dissolved in 20 ml of dry tetrahydrofuran and cooled down at −78° C. under an argon atmosphere is added 1 equivalent of butyl lithium leading to a red heterogeneous mixture to which 1-methyl-4- piperidone (370 mg, 0.40 ml) is added. The cooling bath is removed and the mixture is warmed to 40° C. and the resulting mixture is stirred overnight at 40° C. to obtain a homogeneous and colorless solution which is then evaporated to dryness. The solid residue is taken up in 5% hydrochloric acid from which it crystallizes. Flash chromatography on silica using methanol/dichloromethane 3/97 to 5/95 affords 395.2 mg of the crude title compound. A second chromatography leads to 201 mg of the pure title compound which is crystallized as an oxalate, having a melting point of 246° C.

As stated above, the compounds of this invention are muscarinic cholinergic receptor antagonists, further classified as sub-type $M_1$-antagonists and as such are useful in the treatment of Parkinson's Disease, tardive dyskinesia (i.e. drug induced Parkinsonism in patients treated with neuroleptics) and motion sickness. The compounds of the present invention are used to treat subjects, i.e., mammals such as humans.

Using standard in vitro and in vivo laboratory assay methods and techniques it is to be found that the compounds will exert their $M_1$-antagonist properties in in vitro studies at concentrations of about 0.1 to 1 μM, and in in vivo studies at doses of about 0.1 to 10 mg/kg. Based upon these studies as well as by comparisons with known compounds found to have a beneficial effect for the treatment of Parkinson's Disease, tardive dyskinesia and for motion sickness (functioning via an $M_1$-antagonistic mechanism, it is expected that the compounds will have an end-use application for the treatment of these disease states at daily doses of about 1 to 50 mg. Of course the dosage ranges may be modified by the attending diagnostician depending upon the age and general physical condition of the patient, as well as the severity and duration of the condition to be treated.

In practising the end-use application of the compounds of this invention, the compounds are preferably incorporated in a pharmaceutical formulation comprising a pharmaceutical carrier in admixture with a compound of this invention. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups, emulsions, dispersions and wettable and effervescent powders, and can contain suitable excipients known to be useful in the preparation of the particular type of composition desired. Suitable pharmaceutical carriers and formulation techniques are found in standard texts, such as Remington's Pharmaceutical Sciences, Mack Publishing Company, Easton, Pa., incorporated by reference herein.

Administration of the compounds of the present invention may be by any appropriate method such as administration by mouth including oral, buccal or sublingual, parenteral, transcutaneous, inhalation, or depository forms for body orifices.

Examples of preferred compounds of interest of this invention are:
5-(2'-benzylamino-ethylidene)-5H-dibenzo[a,d]cycloheptene,
5-(2'-N-[N'-methyl-piperazinyl]-ethylidene)-5H-dibenzo-[a,d]-cycloheptene,
5-(2'-N-piperazinyl-ethylidene)-5H-dibenzo[a,d]cyclo-heptene, and
5-(2'-[N-methyl-4-piperidinylidene]-ethylidene)-5H-dibenzo-[a,d]cycloheptene.

What is claimed is:

1. The compound having the following formula or the pharmaceutically acceptable salts thereof

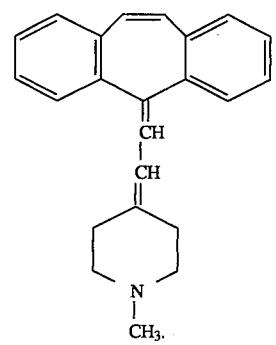

2. A pharmaceutical composition comprising the compound of claim 1 and an acceptable pharmaceutical carrier.

3. A method for treating Parkinson's disease which comprises administering a therapeutically effective amount of a compound of formula 1 or the pharmaceutically acceptable salts thereof to a subject in need of such therapy, formula 1 being

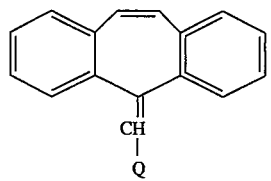

wherein Q is

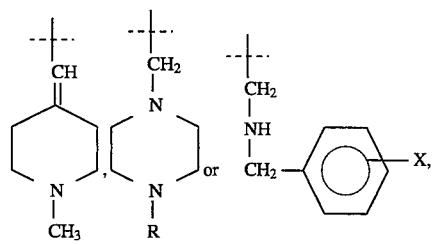

with R being H or $CH_3$, and X is H, $C_{1-6}$ alkyl, halogeno or $C_{1-6}$alkoxy.

4. A method for treating tardive dyskenesia which comprises administering a therapeutically effective amount of a compound of formula 1 or the pharmaceutically acceptable salts thereof to a subject in need of such therapy, formula 1 being
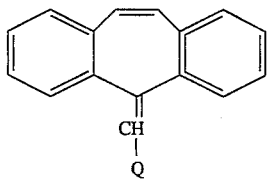
1
wherein Q is
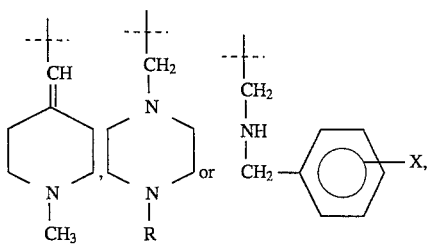
with R being H or $CH_3$, and X is H, $C_{1-6}$ alkyl, halogeno or $C_{1-6}$ alkoxy.
* * * * *